(12) United States Patent
Dorner

(10) Patent No.: US 6,385,287 B1
(45) Date of Patent: May 7, 2002

(54) METHOD AND SYSTEM FOR PROVIDING VIRTUAL GRID FOR PORTAL IMAGING IN A RADIOTHERAPY SYSTEM

(75) Inventor: Karl-Joachim Dorner, Celle (DE)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/732,488

(22) Filed: Dec. 6, 2000

(51) Int. Cl.$^7$ .................................................. A61N 5/10
(52) U.S. Cl. ........................ 378/65; 378/98.4; 378/154
(58) Field of Search ............................ 378/20, 65, 98.4, 378/154, 98.7, 150, 210

(56) References Cited

U.S. PATENT DOCUMENTS

| | | | |
|---|---|---|---|
| 6,094,152 A | * 7/2000 | Cheng | 378/62 |
| 6,097,787 A | * 8/2000 | Siochi | 378/65 |
| 6,208,712 B1 | * 3/2001 | Hernandez-Guerra | 378/150 |

* cited by examiner

Primary Examiner—David P. Porta
Assistant Examiner—T Barber

(57) ABSTRACT

A method and system for providing a portal image of an object utilizing a radiotheraphy system is disclosed. The radiotherapy system includes a system for providing at least one opening over the object. The at least one opening allows radiation therethrough. The method and system comprises acquiring a plurality of images through the at least one opening while moving the at least one opening over the object. Each of the plurality of images includes regions within the opening and regions outside the opening. The method and system includes obtaining a resulting portal image from the plurality of images. Radiation scattered to regions outside the opening is minimized in the resulting portal image to improve image quality. A method and system in accordance with the present invention utilizes a virtual grid to provide a resulting portal image with more contrast. The virtual grid is provided through an opening or a slit. The slit is preferably provided by a plate/jaw system in the radiotherapy system. The plurality of images is provided via the use of software controlling the slit which causes a plurality of images to be provided over an object while the slit is moving over the object. Thereafter, when composing the resulting image, only the regions in the images within the moving slit area are used to compose the result image. The radiation scattered to regions outside the slit do not contribute to the resulting image. A considerable improvement in image quality is thereby provided.

26 Claims, 3 Drawing Sheets

METHOD AND SYSTEM FOR PROVIDING VIRTUAL GRID FOR PORTAL IMAGING IN A RADIOTHERAPY SYSTEM

FIELD OF THE INVENTION

The present invention relates generally to portal imaging in radiotherapy systems and more particularly to improving image quality when providing portal images in such systems.

BACKGROUND OF THE INVENTION

Radiation-emitting, devices are generally known and used for radiation therapy in the treatment of patients, for example. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. During, treatment, the radiation beam is provided on one zone of a patient lying in the isocenter of gantry rotation.

A feature of radiation therapy involves portal images, which are commonly used in radiation therapy to verify and record the patient tumor location. Portal images, i.e., images of the port through the patient through which radiation emerges, include manual (film) and electronic images (EPI) taken before or after the treatment. Electronic portal images (EPI), when taken before the treatment, give the therapist the opportunity of correcting for minor patient positioning errors. Further, EPI allows therapists to take images remotely without going inside the treatment room.

In a typical portal imaging scheme, anti-scatter-grids (placed behind the patient and in front of the film) are used. The grids consist of small lead objects. The lead objects let pass most of the direct radiation from the x-ray source, but they block most of the scattered radiation that is travelling in other directions. In radiotherapy, the penetration of the used high-energy x-ray is so much higher that the anti-scatter grids are only applicable in diagnostics.

In the electronic portal imaging, x-rays are used to see through the body of the patient (for example, to decide if a bone is broken or not). The x-ray source is placed on one side of the patient and a film is exposed on the other side. Inside the patient radiation is attenuated (absorbed and scattered). The radiation is attenuated more by bone than by soft tissue. Therefore, on the film x-ray intensity is less behind a bone. (The aim is to have a big difference in intensity behind bone and soft tissue to have good contrast in the picture.) Scattered radiation reduces the contrast in the images. Current technology using electronic imagers generally provides poor quality images because the contrast is so small, which limits the ability to have electronic images replace film images for the portal radiation field.

Accordingly, what is needed is a method and system for improving the quality of portal images. The present invention addresses such a need.

SUMMARY OF THE INVENTION

A method and system for providing a portal image of an object utilizing a radiotheraphy system is disclosed. The radiotherapy system includes a system for providing at least one opening over the object. The at least one opening allows radiation therethrough. The method and system comprises acquiring a plurality of images through the at least one opening while moving the at least one opening over the object. Each of the plurality of images includes regions within the opening and regions outside the opening. The method and system includes obtaining a resulting portal image from the plurality of images. Radiation scattered to regions outside the opening is minimized in the resulting portal image to improve image quality.

A method and system in accordance with the present invention utilizes a virtual grid to provide a resulting portal image with more contrast. The virtual grid is provided through an opening or a slit. The slit is preferably provided by a plate/jaw system in the radiotherapy system. The plurality of images is provided via the use of software controlling the slit which causes a plurality of images to be provided over an object while the slit is moving over the object. Thereafter, when composing the resulting image, only the regions in the images within the moving slit area are used to compose the result image. The radiation scattered to regions outside the slit do not contribute to the resulting image. A considerable improvement in image quality is thereby provided.

DETAILED DESCRIPTION

The present invention relates generally to portal imaging in radiotherapy systems and more particularly to improving image quality when providing portal images in such systems. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

The present invention relates to integrating automatic exposure control for portal imaging in radiotherapy. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field on a patient. This is by way of example. Thus, the present invention is not intended to be merely limited to the embodiment shown but is to be accorded the widest scope consistent with the principles and features described herein.

Figure 1:
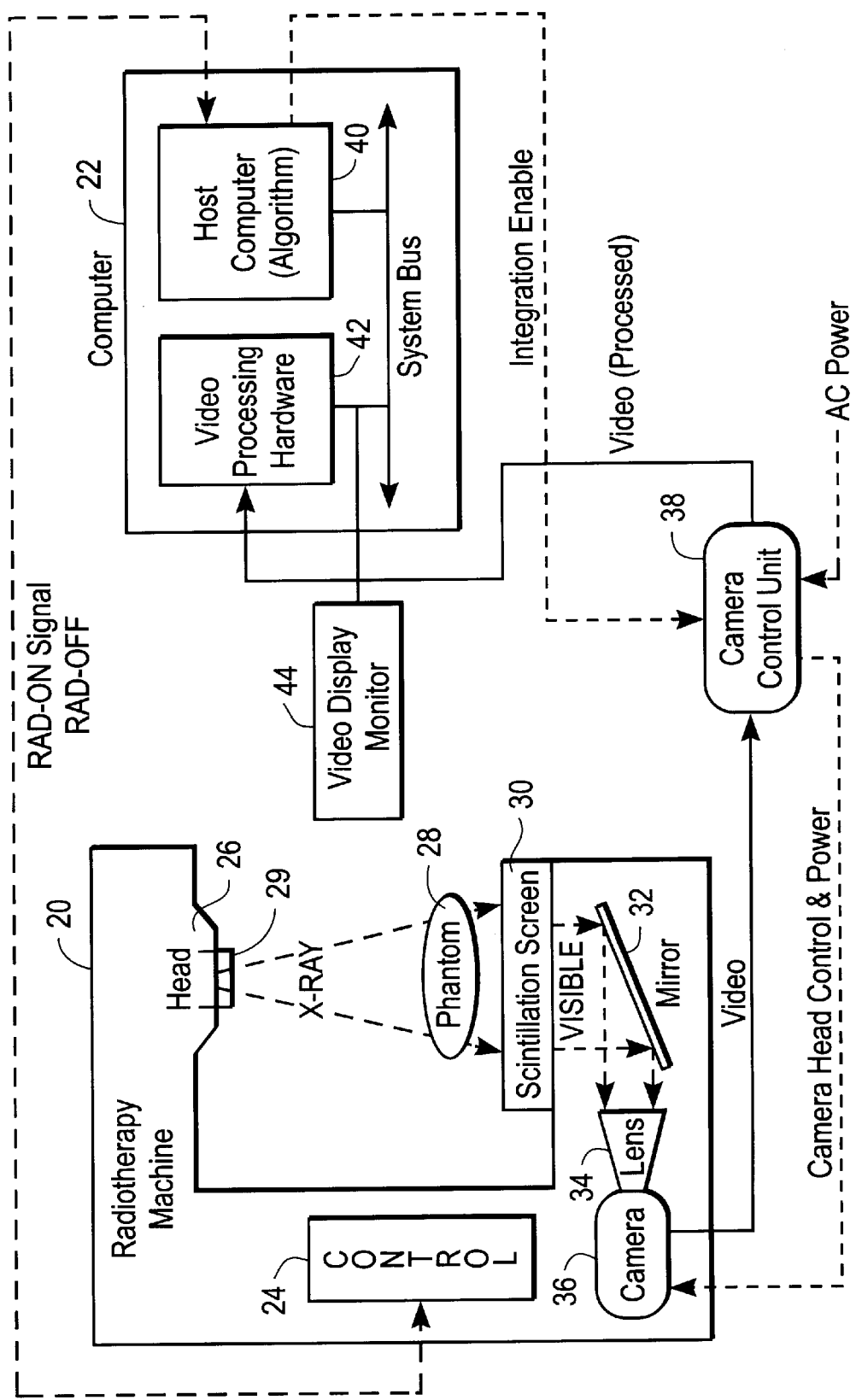
FIG. 1 presents an illustrative radiotherapy system including an electronic portal imager device with portal imaging control in accordance with the present invention.

FIG. 1 presents an illustrative radiotherapy system including an electronic portal imager device with portal imaging control in accordance with the present invention. The device includes a radiotherapy machine 20 controlled by a computer 22, the computer 22 sending signals to a control unit 24 for turning radiation on or off (RAD-ON or RAD-OFF).

The radiation is delivered through a head 26 of the radiotherapy machine 20 to a treatment area 28 of a patient, with delimiting of the field using at least one movable plate/jaw 29 in the beam path, if desired. Imaging of the treatment area 28 occurs by way of a scintillation screen 30, i.e., a radiation detector comprising a metal plate and fluorescent screen, that transfers radiation energy of the treatment beam (X-RAY) passing through the treatment area 28 into visible light energy. The visible light is reflected by a mirror 32 to a lens 34 of a camera 36, e.g., a video camera. A camera control unit 38 provides camera head control and power for the camera 36, as is well understood by those skilled in the art. Further, the camera control unit 38 receives control signals from a host computer portion 40 of the computer 22 and provides video image signals for processing by a video processor 42 of the computer 22 in accordance with the present invention. Processed images are suitably displayed via a video display monitor 44.

The system and method in accordance with the present invention can be provided by a software program resident within computer 22. The software program can be provided via computer readable medium such as a floppy disk, hard drive, DVD, CD-ROM or the like.

A system and method in accordance with the present invention allows for the use of a radiotherapy system to perform portal imaging where the quality of portal images are significantly improved. A virtual grid is provided utilizing an opening or a slit through which radiation is provided to the object of interest. The slit is preferably provided by a plate/jaw system in the radiotherapy system. The plurality of images is provided preferably via the use of software within radiotherapy which allows a plurality of images to be generated over an object while the slit is moving over the object. Thereafter, when composing the resulting image, only the regions in the images within the moving slit area are used to compose the resulting image and the radiation scattered to regions outside the slit during the generating of the plurality of images does not contribute to the resulting image. A considerable improvement in image quality is provided thereby.

Figure 2:
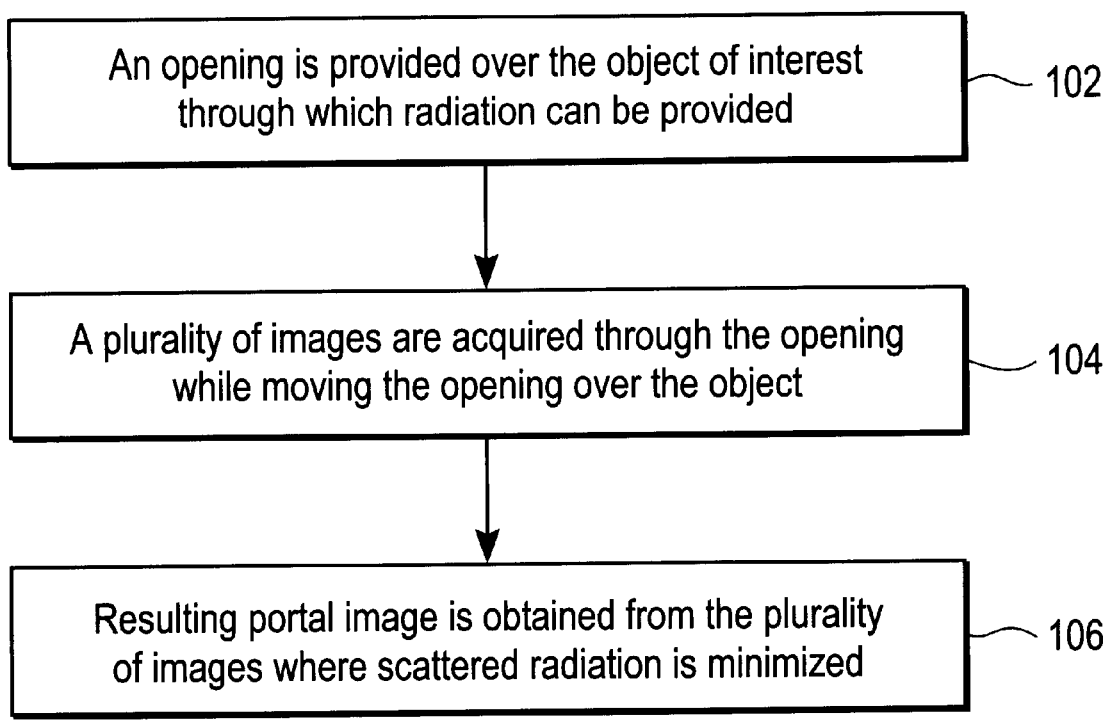
FIG. 2 is a simple flow chart illustrating a method in accordance with the present invention for providing a portal image utilizing a radiotherapy system.

The software program can be provided via computer readable medium such as a floppy disk, hard drive, DVD, CD-ROM or the like. To describe the features of the invention in more detail, refer now to FIG. 2. FIG. 2 is a simple flow chart illustrating a method in accordance with the present invention for providing a portal image utilizing a radiotherapy system. First, an opening is provided over the object of interest through which radiation can be provided, via step 102. Next, a plurality of images are acquired through an opening while moving the opening over the objects, via step 104. Each of the plurality of images includes regions within the opening and regions outside the opening. Next, a resulting portal image is obtained from the plurality of images, where radiation scattered to regions outside the opening is minimized in the resulting portal image to improve image quality, via step 106.

Figure 3:
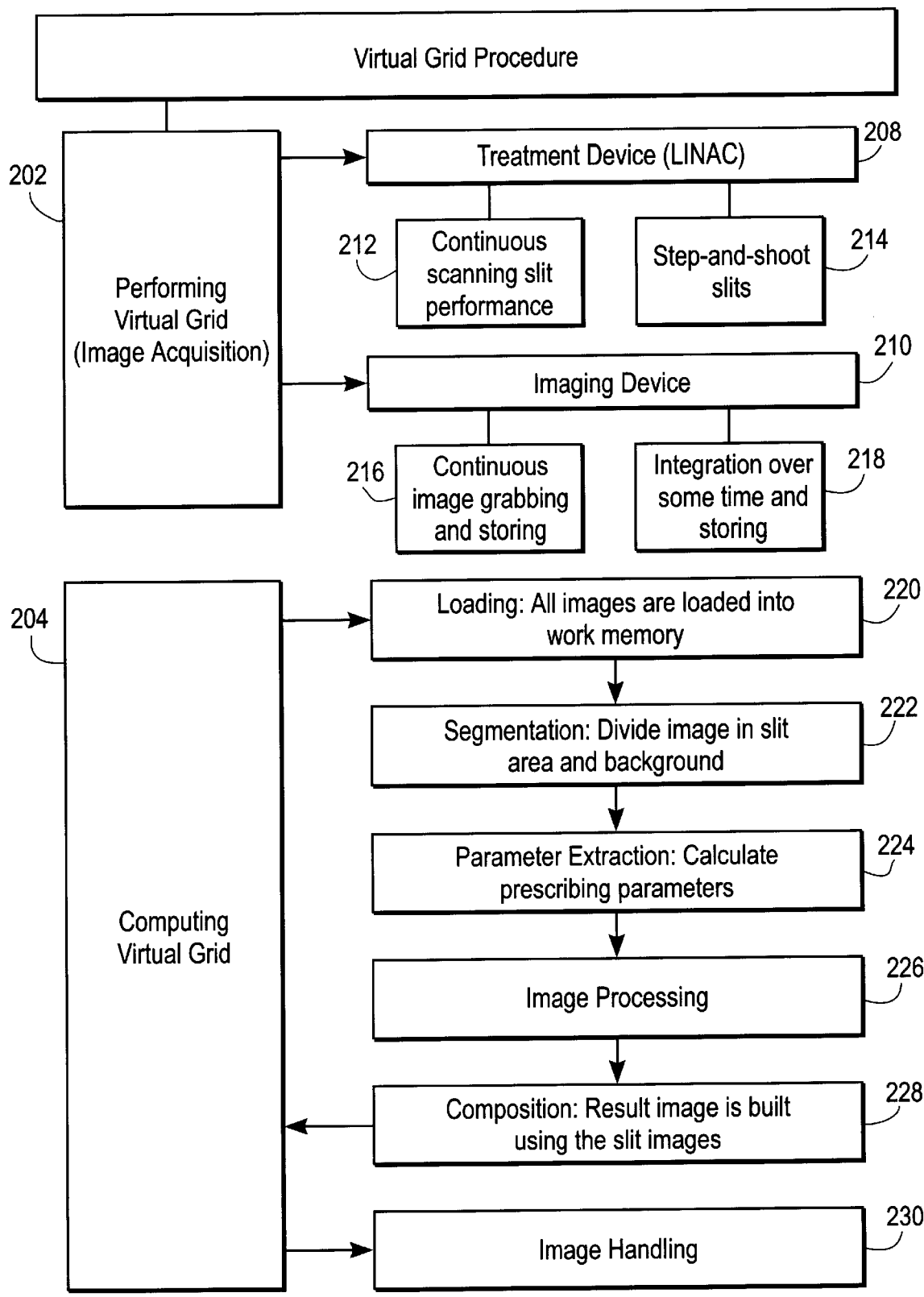
FIG. 3 is a block diagram of a preferred embodiment of a system in accordance with the present invention.

To describe the features of the present invention in more detail, refer now to the following discussion in conjunction with the accompanying Figure. FIG. 3 is a block diagram of a preferred embodiment of a system 200 in accordance with the present invention.

Image Acquisition 202

The following steps describe image acquisition process of the virtual grid system. The image is acquired as illustrated by block 202. The image may be acquired either by a treatment device 208 such as a linear accelerator system manufactured by Siemens Corporation or by an imaging device 210. If the image is acquired by the treatment device 208, image acquisition is accomplished if conventional techniques if continuous scanning of slit performance 212, or step-and-shoot slits 214. On the other hand, if the image is acquired by an imaging device 210, image acquisition can be performed either by continuous image grabbing and storing 216, or integration of (acquired) images over a period of time and storing these images 218.

Computing the Virtual Grid 204

After the images have been acquired, then the virtual grid is computed as illustrated by block 204. The following steps make up the process of computing the virtual grid. First, all the slit images are loaded into work memory, via step 220. Then, each of the slit images are segmented or divided into the slit area and background, via step 222. Next, the prescribing parameters (e.g., Pixel number and image number of contribution pixel, statistics, image processing) are then extracted for each slit image, via step 224. The images are then processed, via step 226, via one or more processes according to the requirements of the particular image. For example, filtering provides noise reduction within the image. The noise reduction can be accomplished, for example, by median filter, time-average-filter or unsharp mask filters. The image can be corrected for slit inhomogenity, changes in pixel-sensitivity, radiation field inhomogenity, distortion corrections, and image warping. The image can also be enhanced for contrast, using filters such as Moving Adaptive Histogram Equalization filter. Any or all of these steps can be utilized to minimize the scattered radiation within the images to improve the quality by providing additional contrast. The resulting image is then composed utilizing the processed slit images, via step 228.

Image Handling 206

The image can then be manipulated in a variety of ways, via step 230, for example, by displaying the image, printing the image, storing the image or further image processing.

Accordingly, a system and method in accordance with the present invention allows for the use of a radiotherapy system to perform portal imaging where the quality of portal images are significantly improved. A virtual grid is provided utilizing an opening or a slit through which radiation is provided to the object of interest. The slit is preferably provided by a plate/jaw system in the radiotherapy system. A plurality of slit images are provided therethrough, while the slit is moving over the object of interest. A resulting portal image is provided from the plurality of slit images where only the regions in the images within the moving slit area are used to compose the resulting image and the radiation scattered to regions outside the slit during the generating of the plurality of images does not contribute to the resulting portal image. As a result, considerable improvement in image quality is thereby provided.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for providing a portal image of an object utilizing a radiotherapy system, the radiotherapy system including a system for providing at least one opening over the object, the at least one opening for allowing radiation therethrough, the method comprising the steps of:

(a) acquiring a plurality of images through the at least one opening while moving the at least one opening over the object; each of the plurality of images including regions within the at least one opening and regions outside the at least one opening; and (b) obtaining a resulting portal image from the plurality of image, wherein radiation scattered to regions outside the at least one opening is minimized in the resulting portal image to improve the quality of the resulting portal image.

2. The method of claim 1 wherein the opening comprises at least one slit in a moveable plate/jaw system.

3. The method of claim 2 wherein the acquiring step (a) further comprises (a1) continuously scanning slit performance.

4. The method of claim 2 wherein the acquiring step (a) further comprises (a1) stepping and shooting the plurality of slit images through the at least one slit.

5. The method of claim 2 wherein the acquiring step (a) further comprises (a1) continuously grabbing and storing the plurality of slit images.

6. The method of claim 2 wherein the acquiring step (a) further comprises (a1) integrating the plurality of slit images over time and storing images.

7. The method of claim 2 wherein the obtaining step (b) further comprises:

(b1) loading a plurality of slit images;

(b2) dividing each of the plurality of slit images into a slit area and a background area;

(b3) extracting prescribing parameters from the plurality of slit images;

(b4) processing the plurality of slit images to minimize the scattered radiation; and (b5) composing a resulting portal image from the scattered radiation minimized plurality slit images.

8. The method of claim 7 wherein the processing step (b4) comprises filtering, correcting and contrast enhancing each of the plurality of slit images.

9. A system for providing a portal image of an object utilizing a radiotherapy system, the radiotherapy system including a system for providing at least one opening over the object, the at least one opening for allowing radiation therethrough, the system comprising:

an image acquisition system for acquiring a plurality of images through the at least one opening While moving the at least one opening over the object; each of the plurality of images including regions within the at least one opening and regions outside the at least one opening; and a virtual grid calculating system for obtaining a resulting portal image from the plurality of images, wherein radiation scattered to regions outside the at least one opening is minimized in the resulting portal image to improve the quality of the resulting portal image.

10. The system for claim 9 wherein the at least one opening comprises at least one slit in a moveable jaw/plate system.

11. The system for claim 10 wherein the image acquisition system comprises a treatment device.

12. The system of claim 10 wherein the image acquisition system comprises an imaging device.

13. The system of claim 11 wherein the treatment device further comprises means for continuously scanning slit performance.

14. The system of claim 11 wherein the image acquisition system further comprises means for stepping and shooting the plurality of slit images through the at least one slit.

15. The system of claim 12 wherein the imaging device further comprises means for continuously grabbing and storing the plurality of slit images.

16. The system of claim 12 wherein the imaging device further comprises means for integrating the plurality of slit images over time and storing the plurality of split images.

17. The system of claim 10 wherein the virtual grid calculating system further comprises:

means for loading a plurality of slit images;

means for dividing each of the plurality of slit images into a slit area and a background area;

means for extracting prescribing parameters from the plurality of slit images;

means for processing the plurality of slit images to minimize the scattered radiation; and means for composing a resulting portal image from the scattered radiation minimized plurality slit images.

18. The system of claim 17 wherein the processing means further comprises means for filtering, correcting and contrast enhancing each of the plurality of slit images.

19. A computer readable medium containing program instructions for providing a portal image of an object utilizing a radiotherapy system, the radiotherapy system including a system for providing at least one opening over the object, the at least one opening for allowing radiation therethrough, the program instructions comprising the steps of:

(a) acquiring a plurality of images through the at least one opening while moving the at least one opening over the object; each of the plurality of images including regions within the at least one opening and regions outside the at least one opening; and (b) obtaining a resulting portal image from the plurality of images wherein radiation scattered to regions outside the opening is minimized in the resulting portal image to improve the quality of the resulting portal image.

20. The computer readable medium of claim 19 wherein the opening comprises at least one slit in a moveable jaw/plate system.

21. The computer readable medium of claim 20 wherein the acquiring step (a) further comprises (a1) continuously scanning slit performance.

22. The computer readable medium of claim 20 wherein the acquiring step (a) further comprises (a1) stepping and shooting the plurality of slit images through the at least one slit.

23. The computer readable medium of claim 20 wherein the acquiring step (a) further comprises (a1) continuously grabbing and storing the plurality of slit images.

24. The computer readable medium of claim 20 wherein the acquiring step (a) further comprises (a1) integrating the plurality of slit images over time and storing images.

25. The computer readable medium of claim 20 wherein the obtaining step (b) further comprises:

(b1) loading a plurality of slit images;

(b2) dividing each of the plurality of slit images into a slit area and a background area;

(b3) extracting prescribing parameters from the plurality of slit images;

(b4) processing the plurality of slit images to minimize the scattered radiation; and (b5) composing a resulting portal image from the scattered radiation minimized plurality slit images.

26. The computer readable medium of claim 25 wherein the processing step (b4) comprises filtering, correcting and contrast enhancing each of the plurality of slit images.

* * * * *